United States Patent
Yoon et al.

(10) Patent No.: US 10,071,128 B2
(45) Date of Patent: Sep. 11, 2018

(54) METHOD FOR PREPARING GRANULES OR PILLS CONTAINING EXTRACTS IN HIGH CONCENTRATION

(75) Inventors: Chil Surk Yoon, Gyeonggi-do (KR); Jai Jun Choung, Gyeonggi-do (KR); Soo Hyun Sung, Seoul (KR)

(73) Assignee: ARIBIO CO., LTD., Sungnam, Gyeonggi-Do (KR)

( * ) Notice: Subject to any disclaimer, the term of this patent is extended or adjusted under 35 U.S.C. 154(b) by 693 days.

(21) Appl. No.: 14/410,054

(22) PCT Filed: Jul. 11, 2012

(86) PCT No.: PCT/KR2012/005510
§ 371 (c)(1),
(2), (4) Date: Dec. 19, 2014

(87) PCT Pub. No.: WO2013/191319
PCT Pub. Date: Dec. 27, 2013

(65) Prior Publication Data
US 2015/0125554 A1    May 7, 2015

(30) Foreign Application Priority Data
Jun. 19, 2012  (KR) .................. 10-2012-0065623

(51) Int. Cl.
| A61K 9/16 | (2006.01) |
| A61K 36/00 | (2006.01) |
| A61K 36/254 | (2006.01) |
| A61K 9/28 | (2006.01) |
| A61K 9/50 | (2006.01) |
| A61K 9/14 | (2006.01) |
| A61K 9/20 | (2006.01) |
| A61K 36/232 | (2006.01) |
| A61K 36/481 | (2006.01) |
| A61K 36/72 | (2006.01) |
| A61K 36/88 | (2006.01) |
| A61K 45/06 | (2006.01) |

(52) U.S. Cl.
CPC .............. *A61K 36/254* (2013.01); *A61K 9/14* (2013.01); *A61K 9/1688* (2013.01); *A61K 9/20* (2013.01); *A61K 9/2866* (2013.01); *A61K 9/5047* (2013.01); *A61K 9/5063* (2013.01); *A61K 36/232* (2013.01); *A61K 36/481* (2013.01); *A61K 36/72* (2013.01); *A61K 36/88* (2013.01); *A61K 45/06* (2013.01); *A61K 36/00* (2013.01)

(58) Field of Classification Search
CPC ... A61K 9/20; A61K 9/14; A61K 9/16; A61K 9/1682; A61K 9/1688
See application file for complete search history.

(56) References Cited

U.S. PATENT DOCUMENTS

2002/0098227 A1    7/2002  Nouri et al.

FOREIGN PATENT DOCUMENTS

| KR | 10-2007-0118020 A | 12/2007 |
| KR | 20070118020 A * | 12/2007 |
| KR | 10-0899334 B1 | 5/2009 |
| KR | 10-2009-0131256 A | 12/2009 |
| KR | 10-0942746 B1 | 2/2010 |

OTHER PUBLICATIONS

Panda RC, Zank J, Martin H "Experimental investigation of droplet deposition on a single particle" Chemical Engineering Journal 83 (2001) 1-5.*
International Search Report for PCT/KR2012/005510 , dated Oct. 29, 2012, 4 pages.
Written Opinion of the International Searching Authority for PCT/KR2012/005510 , dated Oct. 29, 2012, 5 pages.

* cited by examiner

*Primary Examiner* — Christopher Robin Tate
*Assistant Examiner* — Aaron J Kosar
(74) *Attorney, Agent, or Firm* — Lucas & Mercanti, LLP (57) ABSTRACT

The present invention relates to a method for preparing a granule or a pill containing a plant, medicinal herb or traditional oriental medicine decoction extract, comprising the steps of: (a) injecting a powdered plant, medicinal herb or traditional oriental medicine decoction extract into a fluidized-bed device and spraying purified water or a solution of the same type of extract as the extract powder at the extract powder while fluidizing the same, thereby generating microgranules of the extract powder; and (b) injecting the microgranules generated at step (a) as seeds into the fluidized-bed device and spraying a solution of the extract while fluidizing the same, thereby growing the microgranules to a predetermined size of granule or pill. According to the present invention, it is possible to prepare a granule or a pill containing an extract in a high concentration.

7 Claims, 4 Drawing Sheets

(a) Sipjeondaebotang granules (b) Red ginseng concentrate pills (c) Acanthopanax senticosus granules

METHOD FOR PREPARING GRANULES OR PILLS CONTAINING EXTRACTS IN HIGH CONCENTRATION

CROSS REFERENCE TO RELATED APPLICATION

This application is a National Stage of International Application No. PCT/KR2012/005510 with an International Filing Date of 11 Jul. 2012, which claims the benefit of Korean patent application No. 10-2012-0065623 filed 19 Jun. 2012, the entire contents of which are incorporated herein by reference.

BACKGROUND

Technical Field

The present invention relates to a method for preparing granules or pills containing an extract of a plant, herbal medicine, or medicinal herb decoction in a high concentration, and granules or pills containing an extract of a plant, herbal medicine, or medicinal herb decoction in a high concentration, the granules or pills being prepared by the method.

Background Art

Various kinds of extracts, that is, a plant extract, a herbal medicine extract, and a medicinal herb decoction extract, exhibit effects of preventing and treating various diseases and various effects helpful to the human body, such as beauty treatment, immune enhancement, and health promotion. These various kinds of extracts have long been eaten, and have been recognized as medicines with high stability due to having lower toxicity than western medicines which are synthetic medicines, and thus have been variously researched and developed.

With this stream of times, the formulation of extracts has also been actively researched and developed. However, there is no effective solution to the problem in that the contents of effective ingredients in the formulated product of extracts are very low and thus a large dose needs to be taken. More specifically, the herbal medicine extract and the medicinal herb decoction extract are formulated into a liquid dosage form, a granule dosage form, or a pill dosage form, and a large dose of liquid, granule, or pill dosage form is taken at a single dose treatment, 2-4 times a day. Thus, a large amount of medicine needs to be carried and is in convenient to carry around, and a large dose of medicine needs to be frequently taken.

In addition, vegetable extracts, such as an herbal medicine extract and a medicinal herb decoction extract, are difficult to formulate into a dosage form that is easy to take since the content of hydrocarbons, including sugars, such as rhamnose, arabinose, galactose, glucose, xylose, uronic acid, mannose, and galacturonic acid, is very high at 45-65%. That is, the herbal medicine extract, when formulated into a powder, is difficult to handle due to severe moisture retention caused by sugars which are concentrated through the formulation into the powder, and is problematic in long-term storage as a solid dosage form for oral administration and in the maintenance of the stability of the dosage form, the content, and the like, due to a very high degree of moisture retention.

Extract powders, in particular, of Banhasihamtang, *Hovenia dulcis, Allii Bulbus, Rehmanniae* Radix, ginseng, and red ginseng concentrates, which have high contents of sugar and hydrocarbon, have a poor quality stability at room temperature due to moisture absorption thereof, and have a very low degree of fluidity due to the severe moisture absorption thereof, and thus are very difficult in formulation procedures or capsule filling procedures. In the case where other vehicles are added to overcome the problems above, the contents of active ingredients may be lowered more due to the addition of the additives. Thus, conventionally, various kinds of extracts need to be taken in a dosage form of a pill or powder in which the content of vehicle accounts for 60-80% and the content of actual extract is 20-40%.

Meanwhile, the formulation method of an extract according to the conventional art will be described as follows. The spray drying of the extract is a physical method for making a powder. According to the method, a powder product is produced by spraying a liquid sample as small droplets with a size of several tens to several hundreds of micrometers (10-200 µm) and drying the small droplets over high-temperature and hot air for a drying time of 5-30 seconds. This method is employed in 800 or more of pulverizing methods. However, the spray-dried powder has normal problems during the next treatment procedure or in the handling by a user, such as a lot of dust, poor fluidity, easy moisture absorption and oxidation, easy adherence, and poor re-solubility. A powder having high contents of sugar and hydrocarbon, particularly, has strong moisture absorption.

A fluidized-bed device sprays a liquid-phase material toward a top or bottom space from a nozzle, which is installed at the top or bottom of a fluidizing room, to generate particles having a similar shape to a dried product manufactured by spray-drying. At the same time, these particles are allowed to stay in a fluidized state inside the device for a predetermined period of time, so that adhering and coating of the particles by the liquid phase material are repeated, and thus the diameter of the particles becomes gradually increased.

With respect to the procedure for producing a product inside the fluidized-bed device, the liquid phase material is sent to the spray nozzle inside the fluidized room by a peristaltic pump, and then sprayed in a shape of a fog. The solution sprayed from the spray nozzle is dried in a droplet state, thereby generating primary particles. Thereafter, the primary particles adhere to each other by the spray liquid and then are dried, thereby generating particles which are shaped like a bunch of grapes, and the generated primary particles adhere to each other by the spray liquid, thereby growing into circular granules. The grown granule particles repeatedly pass through the vicinity of the spray nozzle, thereby slowly increasing the particle weight and diameter. When the particle diameter increases to some extent, the particles are highly likely to be in contact with the spray liquid material due to the weight of the particle itself, and the spray liquid makes the particles thicker since the surface area of the particles is small. Furthermore, the coating by surface tension for a short period of time before drying and then the drying are repeated, and thus the growth rate of the particles is faster. However, the fluidized-bed device can be normally operated only when certain content or more seeds (assembly) are allowed to stay in the device at the initial operation time to form a fluidized-bed. Various kinds of powders, such as starch, cellulose, and glucose, are used as base seeds (Korean Patent Publication No. 10-2009-0032096). However, on the other hand, these seeds function as an essential ingredient for reducing the content of active ingredient (e.g., extract) of the final product.

In this regard, Korean Patent Application Nos. 10-2007-0063355 and 10-2007-0141999 disclose a method for producing granules and pills using a fluidized-bed device adopting a lower spray manner without using base seeds. The method is characterized in that, when an extract concentrate is sprayed in the fluidized-bed device, the extract concentrate is dried by heat, to form a powder, and the dried powder is used as a seed. However, the power producing capacity and drying efficiency of the fluidized-bed device are very poor at 15-25% even though the fluidized-bed device also has a drying function of a spray drier.

Therefore, with respect to the method for producing granules of an extract using only the fluidized-bed device without base seeds, as described in the above prior patent documents, base seeds for forming an initial fluidized bed need to be primarily formed. However, the fluidized-bed device requires a lot of time due to the low capacity to form a powder, and thus the process efficiency is very low. Since the drying of droplets actually takes a long period of time due to the sugar and the content of sugar contained in a red ginseng concentrate, which is sprayed in the fluidizing room at a temperature 70-85° C., the surfaces of particles are sometimes in a wet state, and the liquid phase material may be coated to flow down on an inner wall of the fluidizing room. In the case where the internal temperature of the fluidizing room is increased to 100-150° C. to overcome the problem above, the drying capacity may be improved. However, the powder which is dried in a manner different from the spray drying is exposed to a high temperature for a long time, and thus may be carbonized. In this regard, Koran Patent Publication No. 10-2009-0032096 discloses a method for preparing spherical granules wherein seeds of 250-750 μm grown by spraying an extract onto various seeds of 200-750 μm and base seeds of 180-250 μm are used as mother granules, and finally spherical granules of 700-1500 μm containing 10-60% of seeds are produced.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY

The present inventors have endeavored to develop a method for preparing granules and pills containing an extract as an active ingredient in a high concentration. As a result, a method for preparing granules and pills capable of containing an extract at a maximum of 100% through a series of processes of primarily preparing microgranules of an extract powder using a fluidized-bed device, using the prepared microgranules as base seeds for fluidized-bed formation, and spraying an extract solution as a binder to the prepared microgranules.

Therefore, an aspect of the present invention is to provide a method for preparing granules or pills containing an extract of a plant, herbal medicine, or medicinal herb decoction in a high concentration.

Another aspect of the present invention is to provide granules or pills containing an extract of a plant, herbal medicine, or medicinal herb decoction in a high concentration (at a maximum of 100 wt %).

Other objects and advantages of the present invention will become apparent from the detailed description to follow taken in conjugation with the appended claims and drawings.

DETAILED DESCRIPTION

In accordance with an aspect of the present invention, there is provided a method for preparing granules or pills containing an extract of a plant, herbal medicine, or medicinal herb decoction in a high concentration, comprising:

(a) feeding an extract powder of a plant, medicinal herb, or medicinal herb decoction into a fluidized-bed device to fluidize the extract powder, and spraying purified water or a solution of the same kind of extract as the extract powder onto the fluidized extract powder, thereby generating microgranules of the extract powder; and (b) feeding the microgranules generated in step (a) as seeds into a fluidized-bed device to fluidize the microgranules, and spraying the solution of the extract onto the microgranules, thereby growing the microgranules into granules or pills with a predetermine size.

The present inventors have endeavored to develop a method for preparing granules and pills containing various kinds of extracts as active ingredients in high concentrations. As a result, a method for preparing granules and pills capable of containing an extract at a maximum of 100% through a series of processes of primarily preparing fine granules of an extract powder using a fluidized-bed device, using the prepared microgranules as base seeds for fluidized-bed formation, and spraying an extract solution as a binder.

Hereinafter, the method of the present invention for preparing granules and pills containing an extract in a high concentration will be described by steps as follows:

(a) Preparation of Microgranules of Extract Powder

In the present step, microgranules of an extract powder of a plant, herbal medicine, or medicinal herb decoction are prepared. More specifically, a extract powder of a plant, herbal medicine, or medicinal herb decoction is fed into a fluidized-bed device and fluidized, and purified water or a solution of the same kind of extract as the extract powder is sprayed onto the extract powder, thereby micro-granulating the extract powder.

As used herein, the term "extract" refers to a substance separated from a liquid or solid mixture by an extraction method which is normally known in the art. In step (a), the extract powder is used.

In step (a), the extract powder may be purchased or may be directly prepared. Therefore, the present invention may further include a step of preparing the extract powder before step (a).

According to a preferable embodiment of the present invention, the extract powder may be prepared by a drying method which is normally known in the art, e.g., hot-air drying, freeze-drying, or natural drying.

According to a more preferable embodiment of the present invention, the extract powder may be prepared by using a spray dryer. The preparation of the extract powder using the spray dryer may be performed under the conditions of an inlet temperature of 145-165° C., an outlet temperature of 75-85° C., and an extract spray rate of 500-1000 d/h, but is not limited thereto.

As used herein, the term "herbal medicine" refers to a natural product that is used as a medicine, as it is, or used as a raw material of pharmaceuticals, and includes (i) medicinal herbs of plants, or (ii) roots, barks, flowers, fruits, seeds, or horns.

In the present invention, the herbal medicine includes Puerariae Radix, Puerariae Flos, Chrysanthemi Flos, Euphorbiae Kansui Radix, Euryalis Semen, Glycyrrhizae Radix, Notopterygii Rhizoma, Zingiberis Rhizoma, Castaneae Semen, Euryales Semen, Platycodi Radix, Sinapis Semen, Cassiae Semen, Galli Stomachichum Corium, Cinnamomi Ramulus, Cinnamomi Cortex Spissus, Ligustici Sinense Radix, Sophorae Radix, Oryzae Fructus Germiniatus, Laminariae Thallus, Pogostemonis Herba, Trichosanthis Semen, Sophorae Flos, Fagopyri Semen, Lycii Fructus, Chrysanthemi Zawadskii Herba, Chinemydis Plastrum, Lumbricus Corpus, Chrysanthemi Flos, Lonicerae Flos, Raphani Semen, Phragmitis Rhizoma, Cervi Cornu, Cervi Pantotrichum Cornu, Aloe, Rhapontici Radix, Salviae Miltiorrhizae Radix, *Angelicae gigantis* Radix, Codonopsis pilosulae Radix, Hordei Semen, Arecae Pericarpium, Rhei Radix et Rhizoma, Illicii Fructus, Euphorbiae Pekinensis Radix, Allii Bulbus, Zizyphi Folium, Persicae Semen, Angelicae Pubescentis Radix, Beninecasae Semen, Malvae Semen, Cordyceps, Eucommiae Cortex, Junci Medulla, Cannabis Fructus, Mate, Hirudonis Caro, Viticis Fructus, Hordei Fructus Germiniatus, Liriopes Radix, Gossypii Semen, Chaenomelis Fructus, Ostreae Concha, Moutan Cortex, Akebiae Caulis, Aucklandiae Radix, Myrrha, Menthae Herba, Pinelliae Rhizoma, Stephaniae tetrandrae Radix, Ledebouriellae Radix, Bombyx Batryticatus, Amomi Rotundus, Amomi Rotundus Fructus, Biotae Semen, Thujae Resina, Atractylodis Rhizoma Alba, Trionycis Carapax, Psoraleae Fructus, Atractylodis Rhizoma, Rubi Fructus, Zedoariae Rhizoma, Eriobotryae Folium, Arecae Semen, Adenophorae Radix, Cnidii Fructus, Amomi Fructus, Croci Flos, Crataegii Fructus, Corni Fructus, Dioscoreae Rhizoma, Zizyphi Spinosae Semen, Zanthoxyli Pericarpium, Scirpi Rhizoma, Taxilli Ramulus, Mori Cortex, Mori Folium, Mantidis Ootheca, Phellini Polyporus, Zingiberis Rhizoma Recens, Haliotidis Concha, Dendrobii Herba, Acori Graminei Rhizoma, Asari herba cum Radice, Cardamomi Fructus, Sappan Lignum, Perillae Fructus, Dipsaci Radix, Pini Pollen, Cynomorii Herba, Cimicifugae Rhizoma, Bupleuri Radix, Massa Medicata Fermentata, Magnoliae Fios, Asini Gelatinum, Agaricus Polyporus, Alpiniae Officinarum Rhizoma, Artemisiae argi Folium, Ligustri Lucidi Fructus, Nelumbinis Semen, Forsythiae Fructus, Rosae Fructus, Ganodermae Polyporus, Acanthopanacis Cortex, Scolopendra Corpus, Aconiti Ciliare Tuber, Trogopterorum Faeces, Mume Fructus, Schizandrae Fructus, Evodiae Fructus, Linderae Radix, Otariae Testis et Penis, Orostachyos Herba, Fossilia ossis Mastodi, Borneol, Gentianae Radix, Bovis Fel, Arctii Fructus, Achyranthis Bidentatae Radix, Coriolus Polyporus, Curcumae Radix, Polygalae Radix, Clematidis Radix, Polygonati Odorati Rhizoma, Ulmi Cortex, Olibanum, Myristicae Semen, Cistanches Herba, Coicis Semen, Epimedii Herba, Alpiniae oxyphyllae Fructus, Lonicerae Caulis, Ginseng Radix, Artemisiae Capillaris Herba, Pterocarpi Lignum, Perillae Folium, Asteris Radix, Hominis Placenta, Paeoniae Radix, Bombycis Excrementum, Jasmin, Polyporus, Scorpio, Peucedani Radix, Bambusae caulis in Taeniam, Phyllostachys Folium, Caryophylli Flos, Houttuyniae Herba, Aurantii Fructus, Lycii Radicis Cortex, Hovenia Semen, Anemarrhenae Rhizoma, Aurantii immaturus Fructus, Sanguisorbae Radix, *Rehmanniae* Radix (*Rehmanniae* Radix et Rhizoma Preparata, *Rehmanniae* Radix Siccus, *Rehmanniae* Radix Preparat), Fraxini Cortex, Tribuli Fructus, Theae Folium, Plantaginis Semen, Xanthii Fructus, Atractylodis Rhizoma, Arisaematis Rhizoma, Cnidii Rhizoma, Gastrodiae Rhizoma, Asparagi Radix, Zanthoxyli Pericarpium, Citrii Unshiu Immaturi Pericarpium, Alpiniae katsumadai Semen, Biotae Cacumen, Aquilariae resinatum Lignum, Gardeniae Fructus, Matricaria chamomilla Linne, Coffee, Alismatis Rhizoma, Cuscutae Semen, Morindae Radix, Crotonis Fructus, Fritillariae Ussuriensis Bulbus, Taraxci Herba, Aconiti Tuber Praepareta, Agaricus Polyporus, Prunellae Spica, Polygoni multiflori Radix, Notarchi Leachii Ovum, Erythrinae Cortex, Eucheumae Thallus, Armeniacae Semen, Cyperi Rhizoma, Elsholtziae Herba, Scrophulariae Radix, Corydalidis Tuber, Nepetae Herba, Scutellariae Radix, Astragali Radix, Phellodendri Cortex, Coptidis Rhizoma, Polygonati Rhizoma, Humuli Flos, red ginseng, Carthami Flos, Magnogliae Cortex, Pireris Nigri Fructus, Siegesbeckiae Herba, Foeniculi Fructus, Glycinis Semen Nigra, and Pharbitidis Semen, but is not limited thereto.

As used herein, the term "medicinal herb decoction" refers to an individual medicine composition by medicinal herbs standard manufacturing process instructions or prescriptions, and includes Sipjeondaebotang, Gamikwibitang, Gamiondanmtang, Sosihotang, Sihamtang, Ongyeongtang, Yukgunjatang, Yijungtang, Cheongseoikgitang, Banhasihamtang, Saenggangsasimtang, Ganghwaryupungtang, Kwibitang, Siryeongtang, and Sihogyejitang, but is not limited thereto.

As used herein, the term "plant" refers to one excluding animals from living organisms constituting a biology system, and more specifically, refers to living organisms that have cell walls and chlorophyll and thus are photosynthetic. The plants included are pine needles, *Taraxacum platycarpum*, mulberry leaves, *Codonopsis lanceolata, Rosa multiflora, Artemisia capillaries, Platycodon grandiflorum, Rubus coreanus Miquel, Artemisia princeps Pamp., Lonicera japonica Thunberg, Adenophora triphylla* var. *japonica*, and *Hovenia dulcis*, but are not limited thereto.

Herein, the binder is sprayed onto the seeds (powder type extract) to form microgranules of a corresponding extract powder through repetitive coating and drying, or and/or form microgranules by binding the extract powder and the extract powder to each other.

According to a preferable embodiment of the present invention, the binder is purified water or a solution of the extract (liquid phase extract), and preferably is a solution of the same type of extract as the extract powder. The content of extract in the microgranule can be raised when the solution of the extract is used as the binder rather than when the purified water is used as the binder.

In step (a) of the present invention, the binder may be sprayed from the top in a top-spray manner, or the bottom in a bottom-spray manner in the fluidized-bed device, and preferably may be sprayed from the top in a top-spray manner in the fluidized-bed device. When the binder solution is sprayed during the fluidizing of the powder, powder particles are liquid cross-linked to each other, and then moisture is evaporated, thereby forming aggregates each composed of three or four powder particles through solid cross-linking. Thereafter, micro-powder particles are continuously linked to each other, thereby forming, so called, raspberry-shaped granules. With respect to the top-spray manner, while a powder moves from the bottom to the top, the binder solution is sprayed downwards from the top in a movement direction of the powder, thereby increasing the frictional force between a droplet and a microparticle caused by increases in the movements of droplets and microparticles in opposite directions and/or the contact frequency between particles, and thus the top-spray manner has a much higher possibility of forming liquid cross-linkage between microparticles than the bottom-spray manner.

In the following examples, microgranules of *Acanthopanax senticosus*, *Astragalus membranaceus*, Banhasihamtang, Sipjeondaebotang, Cheongseoikgitang, *Rehmanniae* Radix Preparat, *Angelica gigas* and *Allium victorialis*, *Hovenia dulcis*, and red ginseng were prepared by spraying extract solutions from the top in a fluidized-bed device in the top-spray manner.

In step (a), the flowing rate of the binder, the nozzle pressure, the hot-air temperature, and the air volume can be controlled in consideration of the viscosity, adhesive strength, and droplet moisture evaporation rate of the liquid material which is sprayed onto the binder. That is, since a liquid material having high viscosity and adhesive strength is easy to become amorphous, the binder is preferably controlled to have a slow flowing rate or be appropriately diluted. Particularly, as for the purified water, the cross-linking force forming function of instantly dissolving and then linking micro powder particles is lost at a high-air temperature and a large air volume since the moisture evaporation is easy, and thus the microgranules are difficult to form. In step (a) of the present invention, the flowing rate of the binder, nozzle pressure, hot-air temperature, and air volume for forming microgranules of the extract powder can be easily determined by a person skilled in the art.

According to a preferable embodiment of the present invention, in the case where the purified water as the binder is sprayed to prepare microgranules, the temperature of the fluidizing room is 70-75° C., the feeding rate of the extract is 100-250 ml/h, and the spray pressure is 0.5 kg/cm$^2$ at an initial state and then may be increased to a range of 0.5-5.0 kg/cm$^2$ while observing the fluidized state. In the case where the extract solution as the binder is sprayed to prepare microgranules, the temperature of the fluidizing room is 65-70° C., the feeding rate of the extract is 100-200 ml/h, and the spray pressure is 0.5 kg/cm$^2$ at an initial state and may be increase to a range of 0.5-5.0 kg/cm$^2$ while observing the fluidized state.

According to step (a) of the present invention, various sizes of microgranules can be prepared, and the diameter of the microgranules generated in step (a) of the present invention is 500 μm or less, preferably 300 μm or less, more preferably 200 μm or less, still more preferably 150 μm or less, still more preferably 1-150 μm, still more preferably 10-150 μm, still more preferably 20-150 μm, still more preferably 30-150 μm, still more preferably 40-150 μm, still more preferably 50-150 μm, still more preferably 60-150 μm, still more preferably 70-150 μm, still more preferably 80-150 μm, still more preferably 90-150 μm; still more preferably 1-120 μm, still more preferably 10-120 μm, still more preferably 20-120 μm, still more preferably 30-120 μm, still more preferably 40-120 μm, still more preferably 50-120 μm, still more preferably 60-120 μm, still more preferably 70-120 μm, still more preferably 80-120 μm, still more preferably 90-120 μm.

Meanwhile, the microgranules generated in step (a) of the present invention may be prepared into tablets through tableting. Here, a vehicle, a coating agent, a lubricant, and/or a disintegrating agent may be used as an additive for preparing tablets to control the molding capability, fluidity, and disintegrability of the microgranules, and can be made into an enteric type highly functional preparation.

Plant type extract powders are impossible to tablet due to moisture absorptivity thereof, but the microgranules generated in step (a) can be used for tableting. Preferably, in the case where the microgranules generated in step (a) are used for tableting, the microgranules are coated with the moisture-proofing coating agent in a content of 1-2% based on the amount of the raw material, and then may be used for tableting.

(b) Preparation of Granules and Pills

In the present step, the microgranules generated in step (a) are fed as seeds for fluidized-bed formation and fluidized, and a liquid phase extract is sprayed to grow the microgranules into granules or pills with a desired size.

A feature of the present invention is to obtain microgranules of the extract-dried powder using a fluidized-bed device, and to feed the obtained microgranules as seeds for fluidized-bed formation, thereby preparing granules and pills. In the case where the microgranules are used as seeds for fluidized-bed formation, the microgranules are highly likely to be in contact with the sprayed liquid material (binder) than the extract powder, and are more thickly coated with the spray liquid than the extract powder due to a small surface area thereof, thereby quickening the growth of the particle diameter by adhering or coating.

According to a preferable embodiment of the present invention, in step (b) of the present invention, the temperature of the fluidizing room is 65-70° C., the feeding rate of the extract is 120-200 ml/h, and the spray pressure is 0.7 kg/cm$^2$ at an initial state and may be increase to a range of 1.0-3.0 kg/cm$^2$ depending on the fluidized state.

According to step (b) of the present invention, granules and pills with a desired size can be prepared. In step (b) of the present invention, the prepared granules has a diameter of preferably 1-3 mm, and the prepared pills has a diameter of preferably 4-10 mm, more preferably 4-9 mm, and still more preferably 4-8 mm.

In step (b) of the present invention, the extract solution as the binder may be sprayed from the top in a top-spray manner, or the bottom in a bottom-spray manner in the fluidized-bed device, and may preferably be sprayed from the bottom in a bottom-spray manner in the fluidized-bed device. The bottom-spray manner is easier in increasing the size of pills and has a higher efficiency of moisture removal and thus achieving more uniform drying than the top-spray manner, and thus can produce more uniform spherical-shaped produce granules and pills without irregular aggregation between particles. In the following examples, granules with a diameter of 2-3 mm and pills with a size of 8 mm were prepared by spraying the extract solution from the bottom in a bottom-spray manner in a fluidized-bed device.

According to a preferable embodiment of the present invention, steps (a) and (b) may be sequentially performed in the same fluidized-bed device equipped with both a top-spray system and a bottom-spray system.

The present invention can preferably produce granules and pills in the same fluidized-bed device through a series of processes of step (a) of generating microgranules in a top-spray manner and step (b) of feeding the generated microgranules as seeds and then spraying a binder from the bottom in a bottom-spray manner.

(c-1) Preparation of Granules and Pills Using Rotor

The present invention may further include: a powder layering step (c-1) of directly binding the microgranule particles of step (a) to surfaces of the granule particles of step (b) via a liquid phase extract using a fluidized-bed device provided with a rotor, after step (b). More specifically, in step (c-1), the granules generated in step (b) are fed as seeds into the rotor of the fluidized-bed device and fluidized, and the extract solution is sprayed to the fluidized granules while the microgranules generated in step (a) are transferred into the rotor, thereby obtaining granules or pills growing to a desired size.

That is, another feature of the present invention is to prepare granules and pills more promptly by feeding the granules generated in step (b) as base seeds into a rotor of a fluidized-bed device equipped with a rotating disk and rotation-fluidizing the granules, feeding the microgranules generated in step (a) from a feeder while the rotor is rotated, and spraying the extract solution as a binder.

According to step (c-1) of the present invention, the sizes of the granules and pills can be increased more promptly and the granules and pills can have a more uniform size when compared with those in step (b).

According to a preferable embodiment of the present invention, the microgranules supplied into the rotor may be coated with a coating agent before being supplied. That is, the microgranules are coated with a coating agent but do not adhere to each other only while the microgranules are transferred into the rotor, and then supplied into the rotor.

A usable coating agent includes ethyl cellulose, methyl cellulose, hydroxypropyl cellulose, polyvinyl pyrrolidone, polyethylene, aquateric, Eudragit™, acrylic coatings, Surelease™, and cellulose acetate phthalate, but is not limited thereto.

Preferably, the microgranules may be coated with ethyl cellulose. That is, the microgranules may be coated with ethyl cellulose of 1-2% based on the weight of the microgranules but do not adhere to each other only while the microgranules are transferred into the rotor, and then supplied into the rotor.

According to a preferable embodiment of the present invention, step (c-1) of the present invention may be performed under the conditions where the rotation rate of the rotating disk is 50-1000 rpm, and preferably 200-800 rpm; the set temperature of the fluidized-bed device is 20-90° C.; the temperature in the rotor is 25-70° C.; the spray rate of the extract solution is 100-500 ml/h; and the spray pressure is 0.5-3.0 kg/cm$^2$, and preferably conditions where the rotation rate of the rotation disk is 250-450 rpm; the temperature of the rotating room of the rotor in the fluidized-bed device is 25-45° C.; and the spray rate of the extract solution is 10 g/min. When the particle size grows with the lapse of time, the rotation rate of the rotating disk, the temperature of the rotating room of the rotor, and the spray pressure of the solvent are gradually increased, thereby controlling the rotating and mixing of rotating particles to be smoothened.

According to a preferable embodiment of the present invention, microgranules with a diameter of 100 μm or less (product in step (a)) and granules with a diameter of 1-3 mm (product in step (b)) may be used in step (c-1).

According to step (c-1) of the present invention, granules and pills with desired sizes can be prepared, and more preferably, the granules and pills prepared in step (c-1) of the present invention have diameters of 1-3 mm and 4-8 mm, respectively.

According to a preferable embodiment of the present invention, steps (a), (b), and (c-1) may be sequentially performed in that order in the same fluidized-bed device equipped with both a top-spray system, a bottom-spray system, and a tangential rotor system.

(C-2) Coating

The present invention may further include, after step (b), coating surfaces of the granules or pills generated in step (b) with a moisture-proofing material (c-2).

In step (c-2) of the present invention, one of various kinds of moisture-proofing coating materials known in the art may be selected and used.

The moisture-proofing coating material includes starch, gelatin, natural food colors, artificial food colors, cellulose, biodegradable polymers, biodegradable oligomers, emulsifying wax, shellac, flavoring agents, hydrophobizing agents or hydrophilizing agents, lipids, proteins, and minerals. Preferably, the moisture-proofing coating material may be at least one selected from the group consisting of hydroxypropyl methylcellulose, hydroxypropyl cellulose, ethyl cellulose, methyl cellulose, titanium dioxide, polyethylene glycol, triethyl citrate, triacetin, dibutyl sebacate, polymethacrylate, cellulose acetate phthalate, carnauba wax, candelila was, petroleum wax, beeswax, and palm oil, but is not limited thereto.

The surfaces of the granules and pills prepared in step (b) or (c-1) of the present invention are coated with a water-proofing coating material, thereby improving stability on storage and stability in the distribution process.

In accordance with another aspect of the present invention, there is provided granules or pills containing an extract of a plant, herbal medicine, or medicinal herb decoction, the granules or pills being prepared by the method of the present invention, wherein the extract is contained in up to 100 wt % with respect to the granule or pill.

Since the granules or pills containing an extract of a plant, herbal medicine, or medicinal herb decoction of the present invention are prepared by the above described method of the present invention, descriptions of overlapping contents therebetween will be omitted to avoid excessive complication of the specification due to repetitive descriptions thereof.

The granules or pills containing an extract of a plant, herbal medicine, or medicinal herb decoction, which are prepared by the method of the present invention, contain an extract as an active ingredient exhibiting a medicinal effect, in a high concentration of 80-100 wt %, preferably 90-100 wt %, and more preferably 98-100 wt %. Therefore, the granules and pills of the present invention can overcome problems of the conventional granules and pills in that a large dose needs to be frequently taken, and thus is inconvenient to carry about since a large amount of medicine needs to be carried. Therefore, the granules and pills of the present invention can be maximally utilized as functional health food, herbal medicines, and various basic processed products.

Advantageous Effects

Features and advantages of the present invention are summarized as follows:

(i) The present invention can produce microgranules and pills with a desired size through processes of primarily obtaining microgranules of an extract dried powder by feeding the extract dried powder as a seed into a fluidized-bed device and then spraying a binder thereonto, and then using the microgranules as base seeds for fluidized-bed formation and spraying a binder thereonto.

(ii) The present invention can produce microgranules and pills with a desired size through a series of processes of spraying a binder in a top-spray manner in the step of preparing microgranules, and spraying the binder in a bottom-spray manner in the step of preparing granules and pills.

(iii) The present invention can produce microgranules and pills with a desired size through processes of feeding granules as seeds into a rotor of a fluidized-bed device and spraying a liquid phase extract while the microgranules are transferred into the rotor.

(iv) According to the present invention, granules and pills containing an extract in a high concentration (at a maximum of 100 wt %).

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Preparation of Extract Powder Through Spray Drying

In the present example, *Acanthopanax senticosus*, *Astragali* Radix, *Angelicae gigantis* Radix and *Allii Bulbus*, *Hovenia dulcis*, and six-year old red ginseng were used as sources for herbal medicine extract samples. For medicinal herb decoctions, decoctions composed of less than 10 species, 10 species, and more than 10 species of raw materials were selected, and corresponding standard decoctions were Banhasihamtang (Pinelliae Rhizoma, Scutellariae Radix, Zingiberis Rhizoma, Adenophorae Radix, Glycyrrhizae Radix, Jujubae Fructus, and Coptidis Rhizoma; seven species), Sipjeondaebotang (Jujubae Fructus, Cinnamomi Ramulus, *Angelicae gigantis* Radix, Adenophorae Radix, Paeoniae Radix Alba, Astragali Radix, Cnidii Rhizoma, *Rehmanniae* Radix Preparat, Atractylodis Rhizoma, and Atractylodis macrocephalae Rhizoma; 10 species); and Cheongseoikgitang (Puerariae Radix, Jujubae Fructus, *Angelicae gigantis* Radix, Liriopis Tuber, Adenophorae Radix, Atractylodis macrocephalae Rhizoma, Cimicifugae Rhizoma, Massa Medicata Fermentata, Phellodendri Cortex, Astragali Radix, Alismatis Rhizoma, Citri reticulatae viride Pericarpium, Atractylodis Rhizoma, Fraxini Cortex, and Schizandrae Fructus: 15 species).

① Preparation of *Acanthopanax senticosus* Powder 5 kg of *Acanthopanax senticosus* and 50 kg of purified water were fed into a herbal extractor, allowed to steep for 2 hours at room temperature, and then extracted for 3 hours at 95° C., followed by filtration. The extract was spray-dried using a spray dryer (SD-1000, Eyela) having an inlet temperature of 150° C., an outlet temperature of 85° C., and an extract spray rate of 500 ml/h. Approximately 900 g of dried powder was prepared per batch of the extract.

② Preparation of *Astragali* Radix Powder 5 kg of *Astragali* Radix and 50 kg of purified water were fed into an herbal extractor, allowed to steep for 2 hours at room temperature, and then extracted for 3 hours at 95° C., followed by filtration. The extract was spray-dried using a spray dryer (SD-1000, Eyela) having an inlet temperature of 160° C., an outlet temperature of 95° C., and an extract spray rate of 1000 ml/h. Approximately 500 g of dried powder was prepared per batch of the extract.

③ Preparation of Banhasihamtang Powder 5 kg of Banhasihamtang prescription raw materials, which were prepared by an oriental medicine clinic, and 50 kg of purified water were fed into a herbal extractor, allowed to steep for 2 hours at room temperature, and then extracted for hours at 95° C., followed by filtration. The extract was spray-dried using a spray dryer (SD-1000, Eyela) having an inlet temperature of 145° C., an outlet temperature of 80° C., and an extract spray rate of 800 ml/h. Approximately 1,050 g of dried powder was prepared per batch of the extract.

④ Preparation of Sipjeondaebotang Powder 5 kg of Sipjeondaebotang prescription raw materials, which were prepared by an oriental medicine clinic, and 50 kg of purified water were fed into a herbal extractor, allowed to steep for 2 hours at room temperature, and then extracted for hours at 95° C., followed by filtration. The extract was spray-dried using a spray dryer (SD-1000, Eyela) having an inlet temperature of 145° C., an outlet temperature of 80° C., and an extract spray rate of 800 ml/h. Approximately 1,250 g of dried powder was prepared per batch of the extract.

⑤ Preparation of Cheongseoikgitang Powder 5 kg of Cheongseoikgitang prescription raw materials, which were prepared by an oriental medicine clinic, and 50 kg of purified water were fed into a herbal extractor, allowed to steep for 2 hours at room temperature, and then extracted for 3 hours at 95° C., followed by filtration. The extract was spray-dried using a spray dryer (SD-1000, Eyela) having an inlet temperature of 145° C., an outlet temperature of 80° C., and an extract spray rate of 800 ml/h. Approximately 950 g of dried powder was prepared per batch of the extract.

⑥ Preparation of *Rehmanniae* Radix Preparat Powder 5 kg of *Rehmanniae* Radix Preparat which was purchased from a herbal medicine shop and 50 kg of purified water were fed into a herbal extractor, allowed to steep for 2 hours at room temperature, and then extracted for 3 hours at 95° C., followed by filtration. The extract was spray-dried using a spray dryer (SD-1000, Eyela) having an inlet temperature of 145° C., an outlet temperature of 80° C., and an extract spray rate of 700 ml/h. Approximately 2,250 g of dried powder was prepared per batch of the extract.

⑦ Preparation of *Angelicae gigantis* Radix and *Allii Bulbus* Powder 5 kg of *Angelicae gigantis* Radix and *Allii Bulbus*, which are mixed at a ratio of 20:80 based on a weight ratio obtained by converting the moisture content of a raw material into 100, and 50 kg of purified water were fed into a herbal extractor, allowed to steep for 2 hours at room temperature, and then extracted for 3 hours at 95° C., followed by filtration. The extract was spray-dried using a spray dryer (SD-1000, Eyela) having an inlet temperature of 145° C., an outlet temperature of 80° C., and an extract spray rate of 800 ml/h. Approximately 2,050 g of dried powder was prepared per batch of the extract.

⑧ Preparation of *Hovenia dulcis* Powder 5 kg of *Hovenia dulcis* and dried fruits thereof and 50 kg of purified water were fed into a herbal extractor, allowed to steep for 2 hours at room temperature, and then extracted for hours at 95° C., followed by filtration. The extract was spray-dried using a spray dryer (SD-1000, Eyela) having an inlet temperature of 145° C., an outlet temperature of 80° C., and an extract spray rate of 800 ml/h. Approximately 1,350 g of dried powder was prepared per batch of the extract.

⑨ Preparation of Red Ginseng Powder 5 kg of 6-year old red ginseng and 50 kg of purified water were fed into a herbal extractor, allowed to steep for 2 hours at room temperature, and then extracted for 3 hours at 95° C., followed by filtration. The extract was spray-dried using a spray dryer (SD-1000, Eyela) having an inlet temperature of 145° C., an outlet temperature of 80° C., and an extract spray rate of 800 ml/h. Approximately 2,600 g of dried powder was prepared per batch of the extract.

Example 2: Preparation of Microgranules in Top-Spray Manner by Fluidized-Bed Device Microgranules were prepared from each of the dried powders prepared in example 1 using a top-spray system of a fluidized-bed device (FBGC-3, Chungjin Tech Korea) provided with the top-spray system, a bottom-spray system, and a tangential rotor system. When the microgranules were prepared in a top spray manner, an extract corresponding to each of the dried powders or purified water was used as a binder. When the extract was used, the fluidizing room temperature was set to 65-70° C., the extract feeding rate to 150-200 d/h, and the spray pressure to 1 kg/cd, and the spray pressure was increased to a range of 1.5-3.5 kg/cd while observing the fluidized state. When the purified water was used, the fluidizing room temperature was set to 70-75° C., the extract feeding rate to 180-250 d/h, and the spray pressure to 1 kg/cd, and the spray pressure was increased to a range of 1.5-3.5 kg/cd while observing the fluidized state. In addition, when the extract was used, 600-1000 g of the corresponding dried powder was fed as a base seed, and when the purified water was used, 1200-1500 g of the corresponding dried powder was fed. For a binder, 1500 g of the corresponding extract was sprayed, and 2000 g of purified water was sprayed in the Banhasihamtang, *Angelicae gigantis* Radix and *Allii Bulbus*, and *Hovenia dulcis*. The results of preparing microgranules by the methods were tabulated in table 1. Samples coated with shellac or ethyl cellulose, shown in table 1, were prepared for tableting in example 5 below, and the sizes of granules and pills were measured after additional processes in the examples below.

TABLE 1

Results of preparing microgranules in top-spray manner and final products thereof

| | | Top-spray process | | | Comparison |
|---|---|---|---|---|---|
| Sample No. | Sample Name | Base Seed (g) | Binder (g) | Microgranule production (g) | Average particle size (μm) | (final product content %) |
| ① | *Acanthopanax senticosus* | 600 | Corresponding extract 1500 | 900 | 100 | Up to 4 mm-sized granules (100%) |
| ② | *Astragali Radix* | 1000 | Corresponding extract 1500 | 1150 | 100 | Up to 2.3 mm-sized granules (100%) |
| ③ | Banhasihamtang | 1500 | Purified water 2000 | 1470 | 80 | Up to 2.3 mm-sized granules (100%) |
| ④ | Sipjeondaebotang | 1000 | Corresponding extract 1500 | 1370 | 100 | Up to 8 mm-sized pills (98.52%) |
| ⑤ | Cheongseoikgitang | 800 | Corresponding extract 1500 | 1080 | 100 | Coated with 1% shellac and then tableted (86.36%) |
| ⑥ | *Rehmanniae Radix Preparat* | 1000 | Corresponding extract 1500 | 1650 | 100 | Coated with 1% ethyle cellulose and then tableted (98%) |
| ⑦ | *Angelicae gigantis* Radix and *Allii Bulbus* | 1500 | Purified water 2000 | 1480 | 80 | Coated with 2% ethyle cellulose and then tableted (85%) |
| ⑧ | *Hovenia dulcis* | 1200 | Purified water 2000 | 1170 | 80 | 2 mm-sized granules containing capsule (100%) |
| ⑨ | Six-year old red ginseng | 1000 | Corresponding extract 1500 | 1750 | 100 | 2 mm-sized granules and 8 mm-sized pills (100%) |

Figure 1:
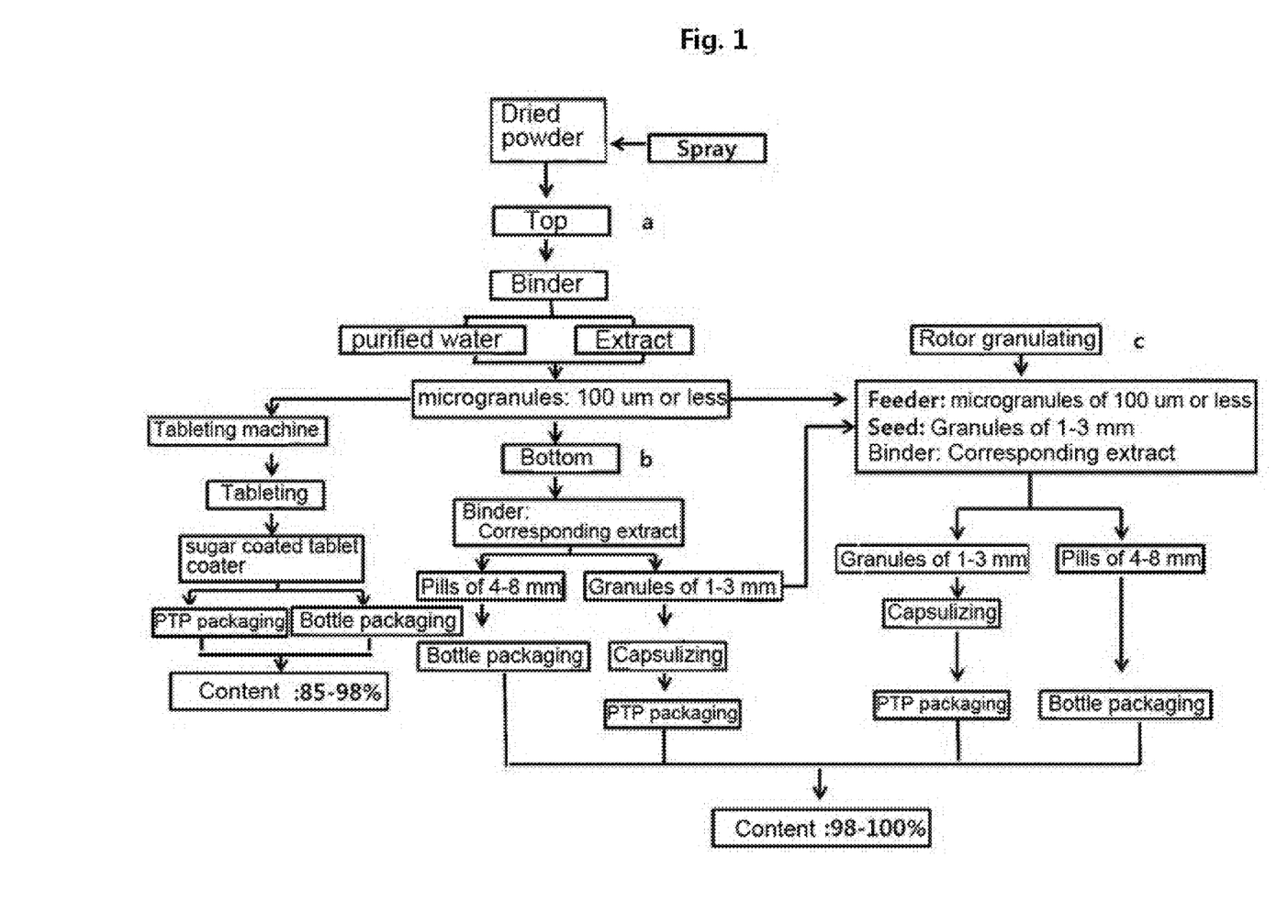
FIG. 1 schematically illustrates a whole flow chart showing a preparing method of the present invention.
Figure 2:
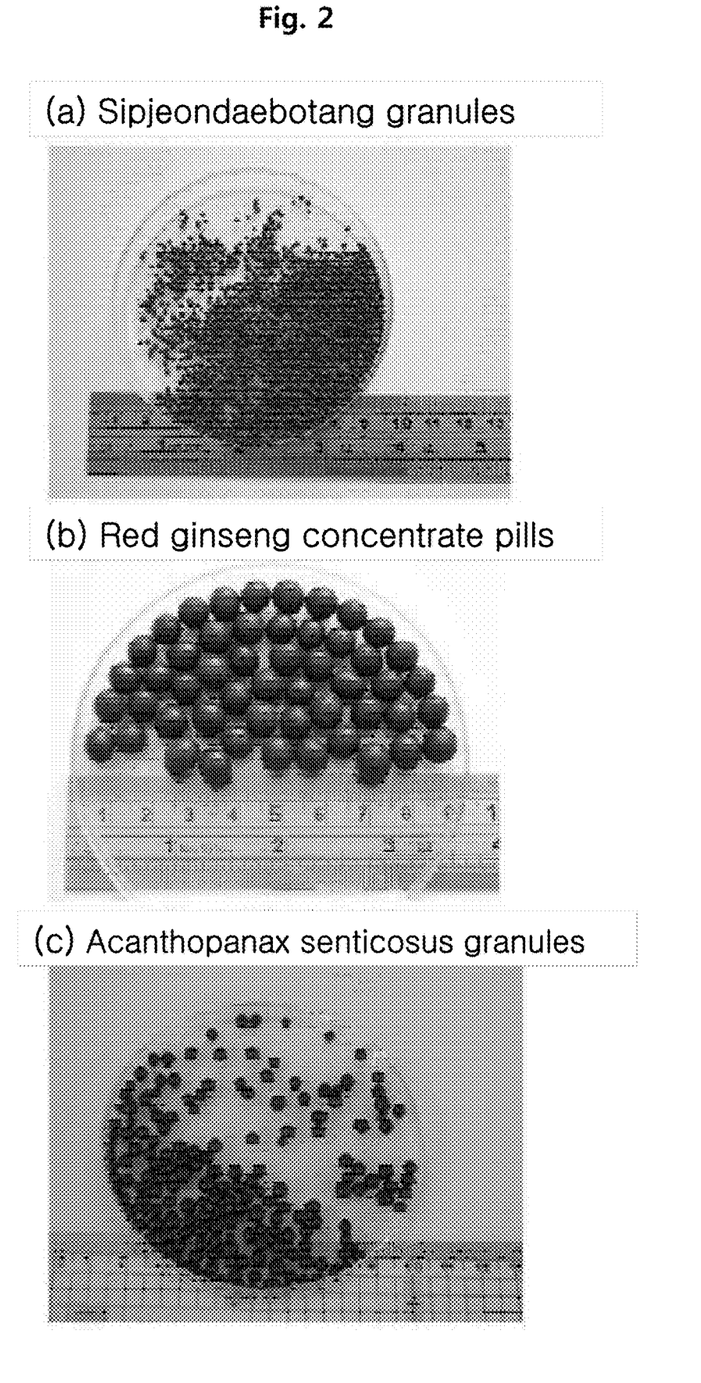
FIG. 2 shows actual images of granules and pills prepared by processes in example 3. (a) Sipjeondaebotang granules; (b) Red ginseng concentrate pills; and (c) *Acanthopanax senticosus* granules

Example 3: Preparation of Granules and Pills in Bottom-Spray Manner by Fluidized-Bed Device The microgranules prepared in example 2 above were fed as base seeds for fluidized-bed formation into the bottom-spray system of the fluidized-bed device (FBGC-3, Chungjin Tech Korea), thereby preparing circular granules and pills. More specifically, 1000 g of microgranules of each of *Astragali* Radix, Banhasihamtang, and *Hovenia dulcis* prepared in example 2 above were fed as base seeds for fluidized-bed formation. The fluidizing room temperature was set to 65-70° C., and the extract feeding rate was increased from 120 ml/h to 200 d/h. The spray pressure was gradually increased from 1 kg/cm$^2$ at an initial state to a range of 1.5-2.0 kg/cm$^2$ while observing the fluidized state. Also, 750 g of microgranules of each of *Acanthopanax senticosus*, Sipjeondaebotang, and red ginseng were fed as base seeds for fluidized-bed formation, to grow the particle size to 3-4 mm. For Sipjeondaebotang and red ginseng, this procedure was repeated one more time, and the spray pressure was increased to 5 kg/cm$^2$ at the maximum limit. In the present process, in order to increase the growing rate of the particle size, the initial solid content (concentration of 5-200) of the corresponding extract was concentrated to 30-400. Through this process, *Astragali* Radix, Banhasihamtang, and *Hovenia dulcis* pills were prepared to have a diameter of 2.3 mm, *Acanthopanax senticosus* and Sipjeondaebotang pills were prepared to have a diameter of 3-4 mm, and Sipjeondaebotang and red ginseng pills were prepared to have a diameter of 8 mm (FIG. 2).

Figure 3:
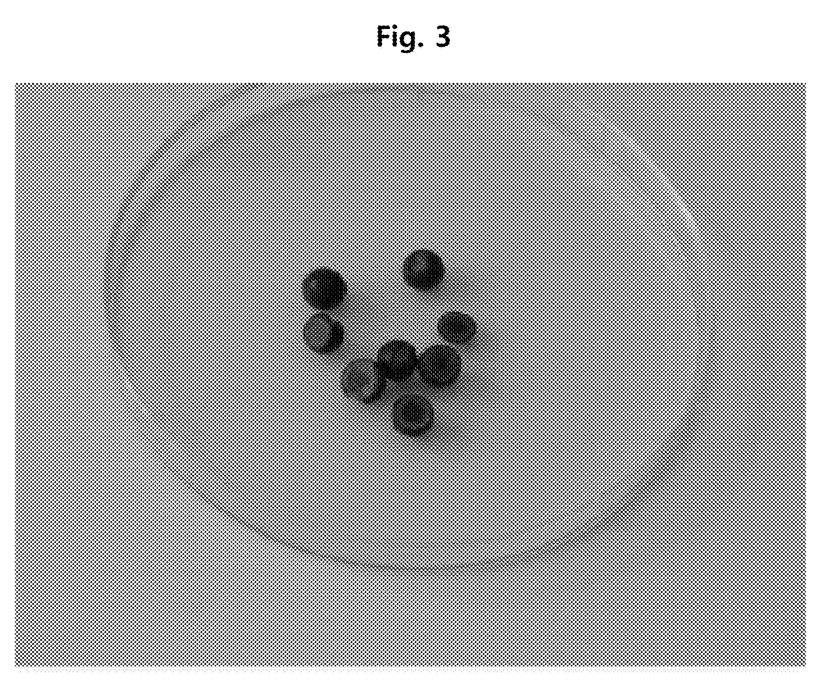
FIG. 3 shows an actual image of Sipjeondaebotang pills prepared by a process in example 4. Dark regions indicate granules with a diameter of 3 mm in the image.

Example 4: Preparation of Granules and Pills Using Rotor System of Fluidized-Bed Device In the preparation of pills using a tangential rotor system of a fluidized-bed device (FBGC-3, Chungjin Tech Korea), Sipjeondaebotang granules with a diameter of about 3 mm prepared in example 3 were used. With respect to the powder constantly fed into the inside of the rotor from the outside, the microgranules prepared in example 2, which was coated with a 1.5% solution in which ethyl cellulose corresponding to 20 based on 1500 g of the microgranules was dissolved in ethyl alcohol, were fed into the rotor at a constant rate using a feeder. That is, 500 g of the granules with a size (diameter) of 3 mm, which was previously prepared in example 3, were fed as seeds into a fluidized-bed rotor system provided with a rotating circular disk, and then the microgranule powder coated with ethyl cellulose was fed into a granulator at a rate of 10 g/min while the rotor system is rotated at 250 rpm. While the internal temperature of the rotor is maintained at 25° C., a Sipjeondaebotang extract prepared in example 1 was sprayed as a binder at a rate of 10 Wmin, thereby growing the microgranules into pills with a size of 8 mm. FIG. 3 shows an image of Sipjeondaebotang pills that have been prepared, and it can be confirmed from FIG. 3 that the microgranule powder is coated in layers on the surface of the Sipjeondaebotang granule with a size of 3 mm (FIG. 3).

Figure 4:
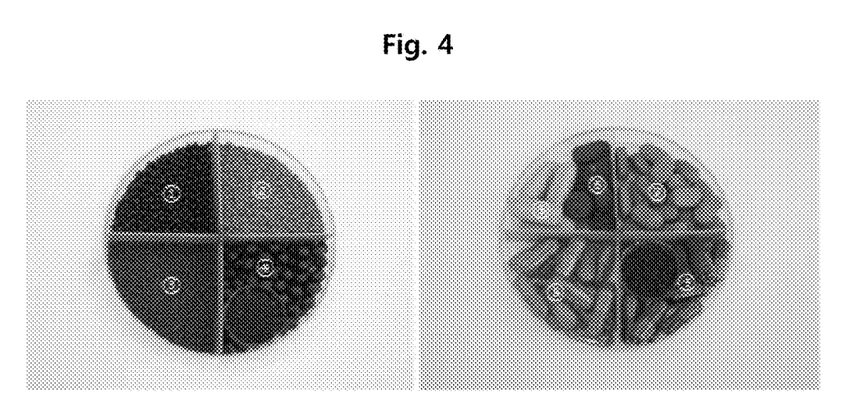
FIG. 4 shows images of final products produced according to the preparing method of the present invention. ① *Acanthopanax senticosus*; ② *Astragalus membranaceus*; ③ Banhasihamtang; ④ Sipjeondaebotang; ⑤ Cheongseoikgitang (rectangular preparation: coated with green color); ⑥ Rehmannia glutinosa (Circular and rectangular preparations); ⑦ *Angelica gigas+Allium victorialis* (rectangular preparation); ⑧ *Hovenia dulcis*; and ⑨ red ginseng.

Example 5: Preparation of Circular and Rectangular Tablets Using Tableting Machine In the last step of the micro-granulating procedure in example 2, the dried powder of each of Cheongseoikgitang, *Rehmanniae* Radix Preparat, and *Angelicae gigantis* Radix and *Allii Bulbus* was surface-coated with a shellac or ethyl cellulose solution, thereby allowing the powder to have improved fluidity in a tableting procedure. Then, raw materials shown in table 2 below were mixed to prepare rectangular and circular tablets. Models KISAN KP-410 and KISAN KF-S50 were used for a tableting machine and a capsule filling machine, respectively. As shown in FIG. 4, it was confirmed that the fluidity was favorable without tangle (cementation) of powder raw materials mixed before tableting, and there were no problems in the moldability for being manufactured into products, binding force, and stability after being manufactured into products.

TABLE 2

Mixing ratio of raw materials for tableting (%)

| Raw material | Cheongseoikgitang | Rehmanniae Radix | Angelicae gigantis Radix + Allii Bulbus |
|---|---|---|---|
| Microgranule powder | 95 | 98 | 85 |
| Avi-cell | 2.5 | 1.0 | 5.0 |
| Saccharose-fatty acid ester | 0.5 | 0.5 | 2.0 |
| stearic acid magnesium | — | — | 5.0 |
| HPMC | 2.0 | 0.5 | 3.0 |
| total, % | 100 | 100 | 100 |
| Note | Coated with gardenia green[a] | — | — |
| Final content (%) | 86.36% | 98% | 85% |

[a] The tablet was externally coated with a 5% solution in which, based on 100 g of a tablet, 5.5% TiO$_2$, 2.5% hydroxypropyl methylcellulose (HPMC), and 2.0% gardenia green are dissolved in 70% ethyl alcohol was prepared, using a sugar coated tablet coater.

Having described a preferred embodiment of the present invention, it is to be understood that variants and modifications thereof falling within the spirit of the invention may become apparent to those skilled in this art, and the scope of this invention is to be determined by appended claims and their equivalents.

The invention claimed is:

1. A method for preparing granules or pills containing an extract of a plant, herbal medicine, or medicinal herb decoction, comprising:
    (a) feeding an extract powder of a plant, medicinal herb, or medicinal herb decoction into a fluidized-bed device to fluidize the extract powder, and spraying purified water onto the fluidized extract powder, thereby generating micro granules of the extract powder, the microgranules having a diameter of 1-150 μm; and
    (b) feeding the microgranules generated in step (a) as seeds into a fluidized-bed device to fluidize the microgranules, and spraying a solution of the same kind of extract as the extract powder onto the microgranules, thereby growing the microgranules into granules having a diameter of 1-3 mm or pills having a diameter of 4-10 mm.

2. The method of claim 1, further comprising, before step (a), preparing the extract powder of a plant, medicinal herb, or medicinal herb decoction in a spray dryer.

3. The method of claim 1, wherein in step (a), the purified water is sprayed from the top of the fluidized-bed device in a top-spray manner.

4. The method of claim 3, wherein in step (b), the solution of the extract is sprayed from the bottom of the fluidized-bed device in a bottom-spray manner.

5. The method of claim 1 further comprising:
    (c-1), after step (b), feeding the granules generated in step (b) as seeds into a rotor of a fluidized-bed device to fluidize the granules, and spraying the solution of the extract onto the fluidized granules while the microgranules generated in step (a) are transferred into the rotor, thereby obtaining granules or pills growing to a predetermined size.

6. The method of claim 1, further comprising:
(c-2), after step (b), surface-coating the granules or pills generated in step (b) with a moisture-proofing material.

7. The method of claim 6, wherein the moisture-proofing material is at least one selected from the group consisting of hydroxypropyl methylcellulose, hydroxypropyl cellulose, ethyl cellulose, methyl cellulose, titanium dioxide, polyethylene glycol, triethyl citrate, triacetin, dibutyl sebacate, polymethacrylate, cellulose acetate phthalate, carnauba wax, candelila wax, petroleum wax, beeswax, and palm oil.

* * * * *